(12) United States Patent
Mahmoud

(10) Patent No.: US 7,992,449 B1
(45) Date of Patent: Aug. 9, 2011

(54) METHOD FOR ASSESSMENT OF CABLE STRENGTH AND RESIDUAL LIFE

(76) Inventor: Khaled M. Mahmoud, Brooklyn, NY (US)

( * ) Notice: Subject to any disclaimer, the term of this patent is extended or adjusted under 35 U.S.C. 154(b) by 352 days.

(21) Appl. No.: 12/372,053

(22) Filed: Feb. 17, 2009

Related U.S. Application Data

(60) Provisional application No. 61/029,040, filed on Feb. 15, 2008, provisional application No. 61/082,554, filed on Jul. 22, 2008.

(51) Int. Cl.
*G01N 3/08* (2006.01)
(52) U.S. Cl. .......................................................... 73/828
(58) Field of Classification Search .................... 73/828
See application file for complete search history.

(56) References Cited

U.S. PATENT DOCUMENTS

| | | | |
|---|---|---|---|
| 2,043,910 A | 12/1932 | Valenzuela | |
| 2,539,954 A | 8/1947 | Hunziker | |
| 4,158,283 A * | 6/1979 | Nation | 57/200 |
| 4,402,229 A | 9/1983 | Byrne | |
| 4,843,372 A | 6/1989 | Savino | |
| 5,365,779 A | 11/1994 | Vander Velde | |
| 5,809,710 A | 9/1998 | Jungwirth et al. | |
| 5,861,557 A | 1/1999 | Sahs | |
| 5,902,962 A | 5/1999 | Gazdzinski | |
| 6,240,783 B1 | 6/2001 | McGugin et al. | |
| 6,312,635 B1 * | 11/2001 | Wang et al. | 264/235 |
| 6,450,036 B1 | 9/2002 | Ashida et al. | |

\* cited by examiner

*Primary Examiner* — Lisa M Caputo
*Assistant Examiner* — Octavia Davis
(74) *Attorney, Agent, or Firm* — Howard Natter; Natter & Natter

(57) ABSTRACT

A method for determining the condition assessment and residual life span of bridge cables based on a parametric statistical model. The method includes random sampling of individual cable wires, mechanically testing the sampled wires, determining the probability of broken and cracked wires and the ultimate strength of cracked wires using fracture toughness and imputing the above data to simulate stress-strain curves for each wire in the cable, applying strain increments until reaching ultimate elongation. Assessing remaining service life of the cable by determining the rate of change of broken wires detected over a time frame, measuring the rate of change of fracture toughness over said time frame, and applying the rates of change to a time-dependent degradation prediction model.

15 Claims, 7 Drawing Sheets

Stress Strain Curve for Wires

METHOD FOR ASSESSMENT OF CABLE STRENGTH AND RESIDUAL LIFE

CROSS-REFERENCE TO RELATED APPLICATIONS

This application claims the benefit of U.S. Provisional Application Ser. No. 61/029,040 filed Feb. 15, 2008 and U.S. Provisional Application Ser. No. 61/082,554 filed Jul. 22, 2008 and incorporates same herein by reference.

FIELD OF THE INVENTION

This invention relates generally to measuring and testing methods and especially to nonlinear analysis for determining the strength of materials.

In particular, the invention concerns a method for condition assessment of bridge cables such as found on suspension bridges and cable-stayed bridges.

BACKGROUND INFORMATION

Suspension bridges typically have two towers defining a main span therebetween and two side spans extending from each tower to respective anchorages at opposite ends of the bridge. Each of the towers supports main cables, extending from an anchorage at one end of the bridge to an anchorage at the other end of the bridge, that constitute the primary load carrying components. The main suspension cables are traditionally constructed by a mechanical process of "cable spinning" whereby spools of high strength galvanized steel wire are secured at each anchorage and spinning wheels pull the wire off the spools. The wire travels from one anchorage, up and over the towers, to the other anchorage. The cable is slidably accommodated in respective saddles mounted on the top of the towers for transfer of the tensile load on the cables to vertical compression load on the towers.

Although most cables are constructed of individual parallel wires, some cables are formed of locked coil strands or helical wires. By way of example, a typical wire diameter, including a zinc coating, is approximately 0.196 in. and has an ultimate strength of approximately 225 ksi. A typical cable of a major bridge generally ranges in diameter from 15 in. up to about 36 in. and consists of from about 5,000 to approximately 28,000 individual wires. The individual wires are tightly wrapped transversely by wrapping wires and restrained from lateral expansion by a radial pressure exerted by the wrapping wires. Vertical suspender or hanger "ropes", attached to each of the main cables by cable bands, support an underlying suspended bridge deck. The distance along the main cable, between the cable bands define panel lengths commonly referred to as "panels". In cable-stayed bridges the cables are attached directly from the towers to an underlying suspended bridge deck.

Suspension bridges, as well as cable-stayed bridges, are usually designed for a service life of 100 years or more. The cables should preferably have a service life comparable to the main structure since replacement of the cables is rarely considered feasible. The cables are however, subject to time-dependent degradation as a result of environmental factors such as hydrogen embrittlement, corrosion fatigue, stress corrosion, cracking, corrosion pitting, and other atmospheric conditions. Additionally, the dead load and the live load, over time, have a detrimental effect on cable strength.

It should therefore be apparent that bridge inspection and maintenance becomes increasingly important as a safety precaution especially as a bridge ages. Furthermore, a method to evaluate the remaining load carrying capacity of the cable and to estimate the residual life span of the cable is of critical importance.

Generally, bridge inspections are focused on visual and subjective evaluation of corrosion damage to the wire surface. Existing cable inspection techniques involve selecting sections of the cables that are judged to be most vulnerable, uncovering the wrapping wires to expose the individual cable wires, separating the cable wires by inserting wedges to allow for visual inspection of the interior wires and then removing a limited number of wires for laboratory testing. The reliability of this method is questionable since only a small portion of a very limited number of wires can be visually inspected and tested. Another shortcoming of this sampling procedure is that it generates a relatively small number of wires within the total population of wires in the cable and further it is not based on a random sampling technique and therefore may not be representative of the larger wire population from which it is drawn. Additionally, the previously known cable strength assessment methods do not always provide reliable information as to cable integrity for the reason that when the cable wires are inspected, even in new condition, there may be small or invisible and thus undetectable cracks that may reduce wire load capacity and/or corroded but unbroken wires that have unknown load capacity. Furthermore, the previously known methods assess the load carrying capacity of the cable based upon measurement of the wire ultimate strength without regard to ultimate elongation and since ultimate elongation is a factor of wire degradation, the omission of this criterion adversely affects the assessment analysis.

It should be further noted that the previous methods for determining cable load capacity also failed to introduce fracture toughness analysis for assessing the strength of cracked wires.

Therefore it should be apparent that currently available cable strength assessment procedures do not provide a well-defined and comprehensive method for cable condition assessment, and do not provide results that are consistent and not dependent on the organization that conducts the evaluation and the effectiveness of the procedure utilized by that organization.

The current technology and assessment methods are therefore of only limited value for providing an accurate evaluation of cable strength and residual cable life. The present invention represents a significant advance in the evolution of techniques for evaluating cable strength and residual cable life.

SUMMARY OF THE INVENTION

Briefly, the nature of this invention concerns a simulation method for generating cable strength and condition assessment data based upon a computational model of an entire wire population of the cable utilizing mechanical property parameters of a sampled number of individual wires.

The method of this invention involves obtaining a random sample of individual wires within a cable panel length including broken, cracked, and intact wires; testing the wire samples under tensile loading for determining mechanical properties including ultimate elongation; determining a maximum elongation threshold based on the ultimate elongation of cracked wires within the sample; segregating the wires based upon the threshold maximum elongation into worst-wire and better-wire proportions; determining the probability of broken wires in the cable based upon the number of observed broken wires within a given panel length; determining the probability of cracked wires in the cable based upon the number of cracked wires in the said sample; applying computational algorithms on worst-wire proportion for establishing a distribution pattern of broken wires and cracked wires in the cable and for indirectly obtaining distribution pattern of intact wires; developing a correlation matrix using the mechanical property variables for the intact and cracked wires in the said sample; simulating the mechanical variables to produce a stress-strain relationship for the intact and cracked wires, based on the properties in the said sample; applying fracture toughness criteria to the cracked wire, for assessing ultimate strength of the cracked wires in the sample; applying incremental strain upon in the simulation model, up to ultimate elongation of each wire and determining corresponding stress; summing up the load carrying capacity of the entire cable.

The method of this invention also provides for an assessment of the remaining service life of the cable by determining the rate of change of broken wires detected by inspection over time and by measuring the rate of change of fracture toughness over said time frame and then applying a time-dependent degradation prediction model.

The individual wires are selected using a random sampling plan that employs a probability method for presenting the best representation and resemblance of wire conditions throughout the entire population of wires in the cable.

A feature of the sampling plan of this invention is that it provides for the determination of an acceptable level of error in the estimated cable strength and minimizes vulnerabilities introduced in the cable cross-section due to the removal of the sampled wires.

Another aspect of this invention is that it incorporates ultimate elongation as a factor in determining wire load capacity.

A further aspect of this invention is the application of fracture toughness for assessing the ultimate strength of cracked wires.

Still another aspect of this invention is that it also provides an assessment of remaining service life of the cable.

Having thus summarized the invention, it will be seen that it is a preferred object thereof to provide a random sampling plan and simulation method and model for assessing cable strength of the general character described herein which is not subject to any of the previously mentioned limitations.

Another preferable object of this invention is to analyze cable strength based on a parametric statistical model of the strength of individual wires in the cable.

Still another preferred object of this invention is to select the individual wires for testing using probability sampling wherein the sampling error can be calculated.

Yet another preferred object of this invention is to provide a simulation method and model for assessing cable strength that characterizes both the damage induced on the cable by the degradation process and the true behavior of the cable wires.

A further preferred object of this invention is to establish a consistent methodology for utilizing inspection findings and laboratory test results for standardizing condition assessment and reliability updating.

Another preferred object of this invention is to incorporate wire ductility for classifying wires within the cable based on ultimate elongation.

Still yet a further preferred object of this invention is to estimate the residual life span of the cable as environmental degradation evolves with time by considering degradation kinetics.

To these and to such other preferred objects which may hereinafter appear, the present invention relates to a method for assessment of cable strength and residual life especially as applied to bridge cable as set forth in detail in the following specification and recited in the annexed claims, taken together with the accompanying drawings.

BRIEF DESCRIPTION OF THE DRAWINGS

In the accompanying drawings in which are shown exemplary illustrations of the method of this invention.

DETAILED DESCRIPTION OF THE INVENTION

With specific reference now to the drawings, it is stressed that the particulars shown and described herein are for the purpose of illustrative discussion of the process of this invention and are presented in the cause of providing what is believed to be the most useful and readily understood description of the principles and conceptual aspects of this invention. In this regard, no attempt has been made to show the process in more detail than is necessary for a fundamental understanding of the invention however, the description, in combination with the drawings, should make apparent to those skilled in the art how the process may be applied in practice.

Figure 1:
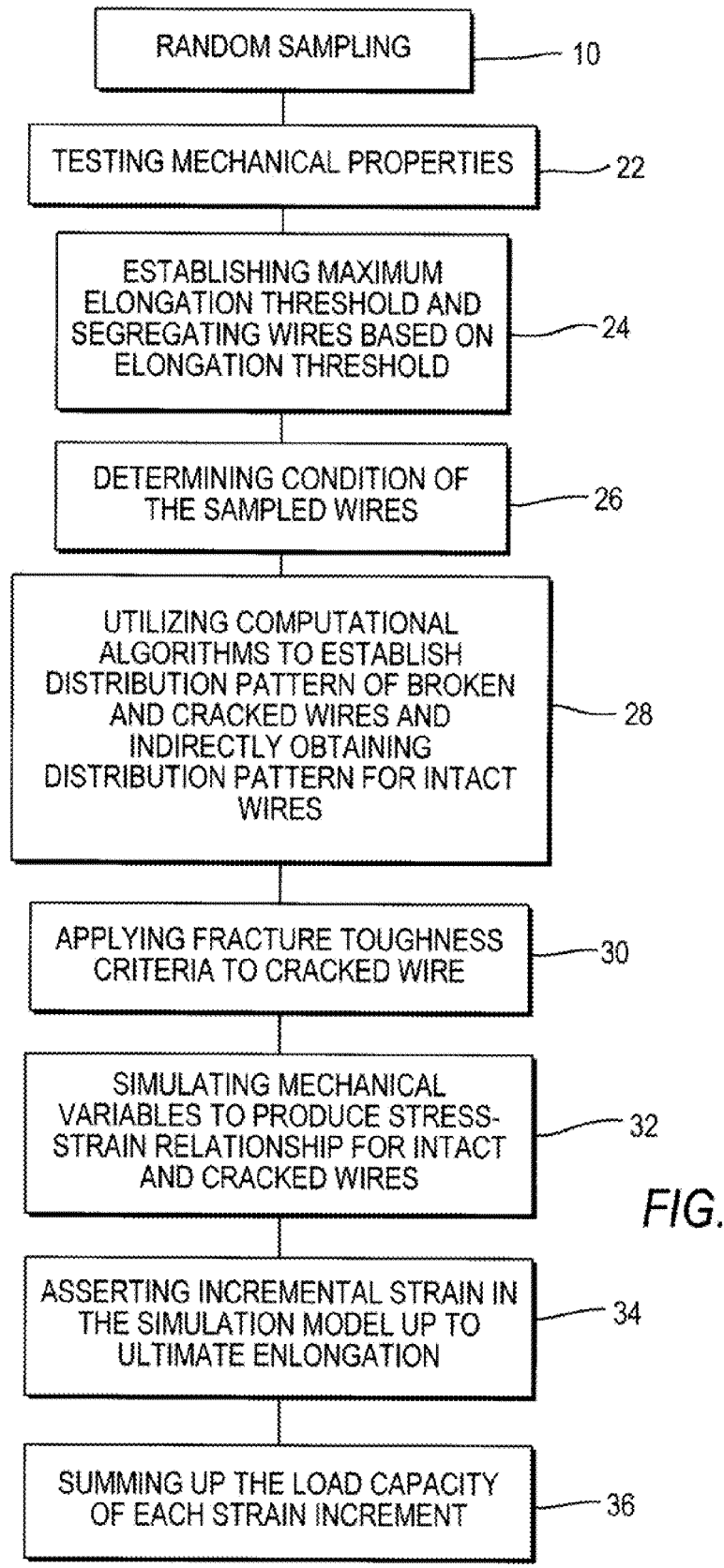
FIG. 1 is a flowchart illustrating the simulation method of this invention.

The invention will now be described with reference to the flowchart of FIG. 1. The initial step, as shown in FIG. 1, is the random sampling of the wires within the cable denoted at 10 that takes place during inspection of the cables. The purpose of the inspection is to detect cable deterioration sites and to preferably remove sample wires at these sites.

In accordance with the sampling method of this invention a sampling frame is defined as the accessible group of wires from which sampled wires will be randomly selected. The sample size is defined as constituting the number of sampled wires from which valid conclusions about the entire population of wires in the cable can be made and to which a statistical inference can be applied for inferring the degraded condition of all the wires in the cable from those wires found in the sampled wires. By virtue of the random selection of the sampled wires the different conditions of the wires will be encountered in the sampled wires, e.g. intact wires, broken wires, cracked wires.

Figure 2:
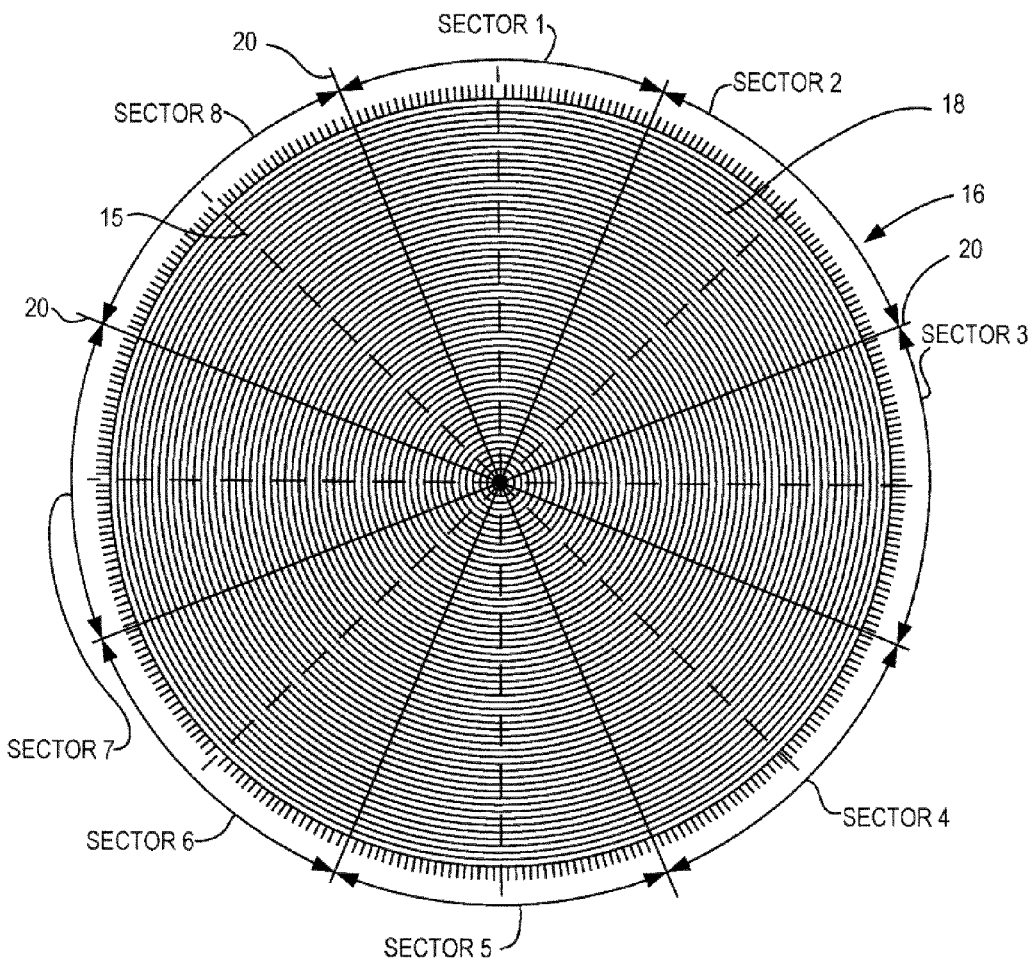
FIG. 2 is a diagrammatic cross-sectional view of a typical cable with the wrapping wires removed and showing a pattern of concentric rings depicting the cumulative cross-sections of the individual wires within the cable, with the cable being divided into eight sectors by radial lines defining the location of wedge openings.
Figure 3:
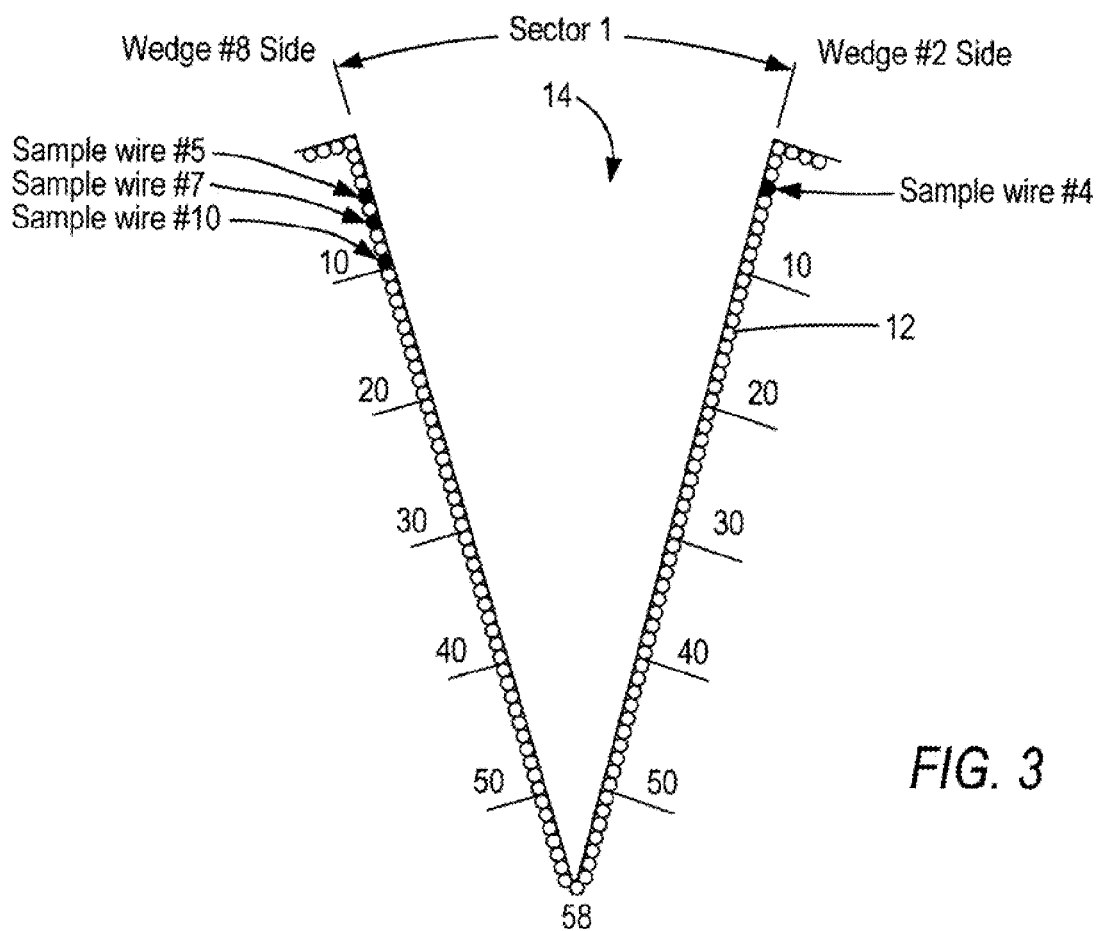
FIG. 3 is an enlarged diagrammatic cross-sectional view showing a typical wedge opening extending along a longitudinal axis of the cable and exposing the individual wires.
Figure 3A:
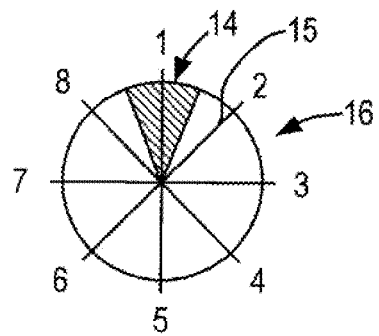
FIG. 3A is a diagrammatical illustration showing the orientation of the wedge openings of FIGS. 2 and 3.

Further with regard to the procedure for obtaining sample wires from a cable 16 in selected cable panels, first the wrapping wires are removed along a longitudinal length of the cable 16 to expose the individual wires 12. Referring now to FIG. 2, there is diagrammatically shown a cross-section of the cable 16 containing a pool of exposed wires represented, in cross-section, by concentric rings 18 that are, for the purposes of illustration, numbered at every $10^{th}$ ring counted inwardly toward the center wire. The ring numbering is also shown in FIG. 3. It should also be observed that the cable 16 is divided into uniformly spaced sectors identified as sectors 1 though 8 and defined by radial lines 20, thus forming a typical eight-wedge pattern. The procedure involves inserting and driving the wedges into the wires 12 along a respective wedge line 15 resulting in a plurality of peripheral wedge openings 14, one which is graphically demonstrated in FIG. 3. The wedge opening 14 may typically extend along the longitudinal axis of the cable 16 at the 6:00 o'clock, 4:30 o'clock, 7:30 o'clock, 3:00 o'clock, 9:00 o'clock, 1:30 o'clock, 10:30 o'clock and 12:00 o'clock positions, as shown in FIG. 2. By way of example, the wedge opening 14, shown in FIG. 3, is located at sector 1 in FIG. 3A. Note particularly with regard to FIG. 3, which shows the wedge opening 14, that for practical reasons that will be discussed herein the sampling frame is preferably limited to the first 10 to 15 of the rings 18 of the exposed wires 12, approximating a depth of 2-3 inches. The sampling procedure further includes assigning an identification number (I.D. no.) to the wedge opening 14, including coding for differentiating between the sides of the wedge opening 14, and also assigning an I.D. no. for identifying the individual wires 12 within the wedge opening 14. For example, in FIG. 3 the wedge opening 14, is located in sector 1, and is identified by the two flanking wedge lines 15; i.e., wedge 2, designating wires to be sampled on the east side, and wedge 8, designating wires to be sampled on the west side of the wedge opening 14. The specific wire 12 to be sampled is identified by the corresponding concentric ring number. Thus in FIG. 3, the three sample wires on the left or west side (wedge #8 side) are denoted as sample wire #5, sample wire #7 & sample wire #10 on wedge #8 side. The sample wire on the right or east side of the wedge opening 14 (wedge #2 side) is denoted as sample wire #4 on wedge #2 side. The cable wires 12 to be sampled are then selected utilizing a computerized random number generator and removed from the cable 16 for laboratory testing.

It should also be observed that sampling consistency is achieved by standardizing the following at each of the panels: the same wedge pattern is used in each of the panels; the same longitudinal length of wedge opening is used in each of the panels; at each panel the wires are sampled from the same sampling frame (for example the first ten rings of wire) and further the sampling from each panel should be conducted during similar weather conditions to eliminate the effect of rain, extreme heat and humidity on the physical properties of the cable and on the performance of the inspectors and the contractor's crew.

The effect of sample size on acceptable level of error in the estimated cable strength will now be discussed. The error results from statistical imprecision associated with estimating nominal cable strength based on a limited number of wire samples. Therefore a target for an acceptable level of error is set in determining the estimated cable strength. According to Article 3.4 of the *NCHRP Manual for Condition Evaluation and Load Rating of Highway Bridges Using Load and Resistance Factor Philosophy*[a], the minimum expected finite fatigue life is taken as the fatigue resistance two standard deviations below the mean fatigue resistance. This is equivalent to a 97.73% one-sided confidence level. By way of example, the method of this invention establishes a target for the acceptable level of error in the estimated cable strength, e.g. 5% with a 97.73% level of confidence, which corresponds to two standard deviations below the mean cable strength. It should be apparent that other acceptable level of error standards may be used as deemed necessary.

[a]*Manual for Condition Evaluation and Load Rating of Highway Bridges Using Load and Resistance Factor Philosophy*, NCHRP Project C12-46, May 2001.

Figure 4:
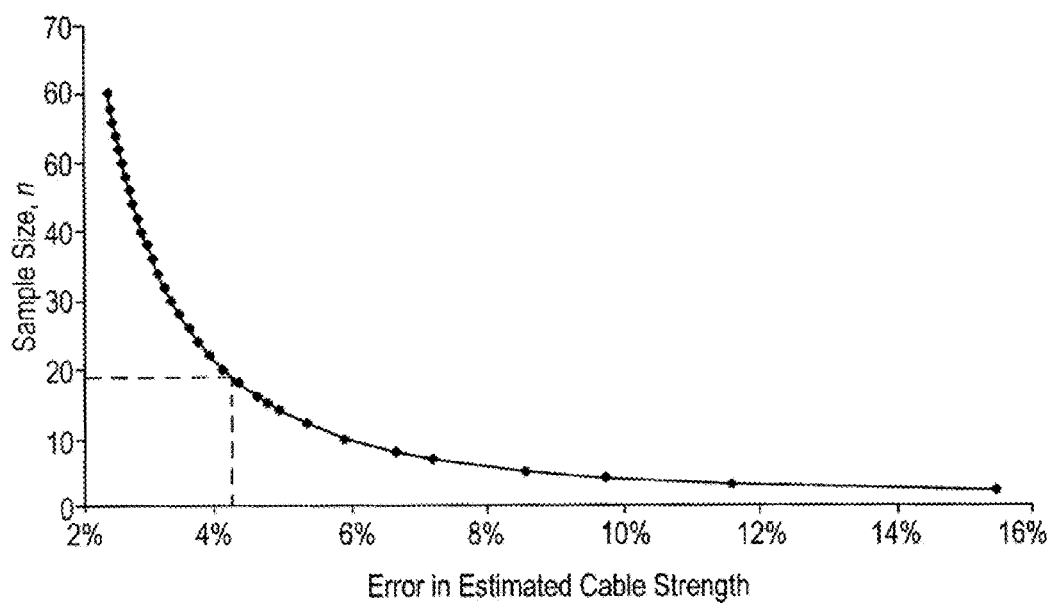
FIG. 4 is a graphical representation showing sample size effect on acceptable level of error in estimated cable strength at 97.73% level of confidence in cable comprised of intact wires.
Figure 5:
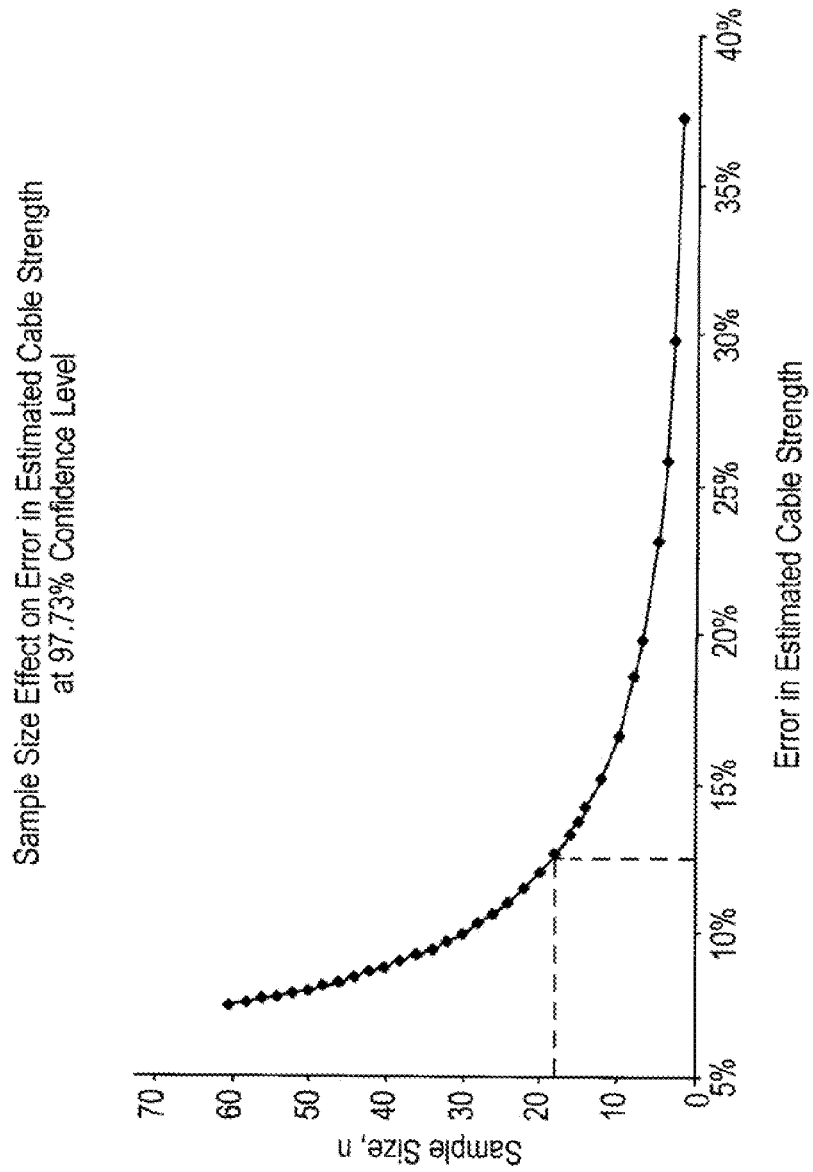
FIG. 5 is a graphical representation illustrating sample size effect on acceptable level of error in estimated cable strength at 97.73% level of confidence in cable comprised of cracked wires.

In this typical example, a sample size is determined to limit the acceptable level of error in the estimated cable strength to 5% with 97.73% level of confidence. Use is made of existing sets of data from previously tested degraded bridge wire samples with the available wire strength data being fitted to a Weibull distribution. The variance of estimated cable strength, which is a function of sample size, is derived from the means, variances, and covariance of estimators of the Weibull distribution parameters for intact wires is shown in FIG. 4 and for cracked wires as shown in FIG. 5. A sample size is then determined for achieving a desired target acceptable level of error of 5% at 97.73% level of confidence for intact wires. Referring now to FIG. 4 it is noted that a sample size, n=18, corresponds to 4.24% level of error in cable strength at 97.73% level of confidence within a cable of intact wires. Similar analysis of cracked wire data reveals that a sample size of, n=18 (FIG. 5), corresponds to 12.18% level of error in the estimated cable strength at 97.73% level of confidence for a cable comprised of cracked wires. In a cracked wire proportion of 0.1%, and the level of error assessed from FIGS. 4 and 5, the level of error in the estimated cable strength is evaluated at 4.9% that is, less than 5% at 97.73% level of confidence, therefore the 18 sampled wires meet the target criteria and represent an appropriate sample size.

The sampling method further recognizes the following practical considerations:
- It is not feasible to remove wires too deep in the wedge opening due to clearance problems with the remaining wires within the wedge opening when cutting, splicing and re-tightening the wire.
- Even if a deeper wire is pulled with the use of a special tool out of the wedge, access for splicing and re-tightening would be very limited and damage to neighboring wires would become more likely.
- It is therefore recommended to minimize damage to the main cable by not removing samples from areas where they could not effectively be replaced and spliced.
- Outer wires are easily accessible, however, inner wires are difficult to reach for the purpose of tightening the ferrules used to splice replacement wires, and often a wire would be spliced with zero or small stress.

The next step of the process, designated at 22 in FIG. 1, involves testing the mechanical properties of the sample wires 12. A mechanical tension test is performed, preferably in accordance with ASTM E8 specifications. The testing will provide the yield strength, $\sigma_e$; ultimate strength $\sigma_u$; and ultimate elongation $\epsilon_u$ as measured along a gage length as well as the Young's modulus E. Each of these four variables represents physical properties of the wire and since they can cover a range of values they are treated as random variables. The variation of each is measured by the mean and the standard deviation and a probability distribution is then assigned for each random variable. A Log-Normal, Weibull or equivalent distribution technique may be used to describe the range for each of these variables.

The procedure then establishes an elongation threshold, shown at 24 in FIG. 1, whereby the wire samples 12 are segregated into a "worst-wire proportion" and a "better-wire proportion". The threshold elongation ($M_{threshold}$) is established by obtaining the ultimate elongation of cracked wires. To establish the threshold elongation, at a certain level of confidence, use is made of the mean, $\mu$, and the standard deviation, $\sigma$, of the ultimate elongation of cracked wires, obtained from laboratory test data. For a one-tailed distribution at 99.5% level of confidence, the threshold elongation, $M_{threshold}$, is established using the following formula:

$$M_{threshold} = \mu + 2.58\sigma.$$

That is to say that there is 0.5% chance that the ultimate elongation of a cracked wire will exceed $M_{threshold}$, at 99.5% level of confidence.

The threshold elongation, $M_{threshold}$, is assumed to divide the entire wire population into two different proportions, the worst-wire proportion of wires having ultimate elongation below $M_{threshold}$ and the better-condition wire proportion or wires that have an ultimate elongation higher elongation than $M_{threshold}$. The worst-wire proportion $P_{worst}$ contains all cracked and broken wires as well as some intact wires that exhibit an elongation lower than the threshold elongation. Using the above criterion, $P_{worst}$, is established from the available test data for each panel. All specimen wires with maximum elongation less that the threshold elongation, $M_{threshold}$, divided by the total number of specimen wires defines, $P_{worst}$ as a percentage of the total specimen wires.

The next step, denoted at 26 in FIG. 1, is determining the condition of the wires within the sample. The wires may be found broken, cracked or intact. The possible outcome of the condition of a wire as broken, cracked or intact is treated as a discrete random variable, X, in accordance with the following formula:

$$P\{X = x_j\} = P_j, \; j = 0, 1, 2, \; \sum_{j=0}^{2} p_j = 1$$

where $x_0$, $x_1$, and $x_2$ represent in this case broken, cracked and intact wire respectively and $p_0$ is the probability of realizing a broken wire, $p_1$ is the probability of realizing a cracked wire, and $p_2 = 1 - p_0 - p_1$ is the probability of having an intact wire. The probability of broken wires, $p_0$, in each panel is determined based on the number of wires found to be broken. The probability of cracked wires, $p_1$, is determined from assessing the ratio of cracked wires in the sample.

A mathematical simulation technique, such as the Monte Carlo method, is then used to establish the distribution pattern of broken and cracked wires within the panel from which the sample wire was obtained as indicated at 28 in FIG. 1. The input variables used in the simulation program are the probability of broken wires, ($p_0$), the probability of cracked wires ($p_1$) and the percentage of worst-wire population ($P_{worst}$) to the total wires in the sample. The distribution pattern of intact wires is then indirectly obtained based on the above results.

Figure 6:
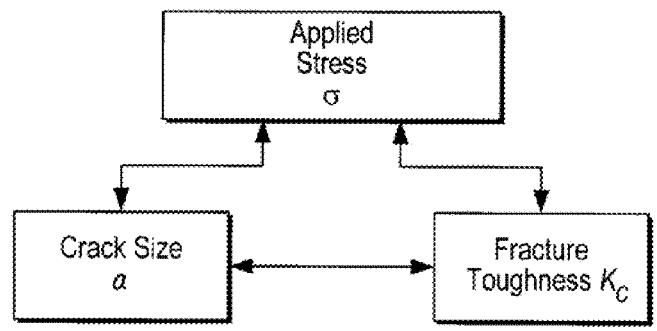
FIG. 6 is a fracture mechanics triangle that illustrating the relationship between the three variables, applied stress, crack size, and fracture toughness.

In order to determine the ultimate capacity of a cracked wire, the method of this invention introduces a fracture-based analysis providing a mathematical relationship between the variables of applied stress ($\sigma$), crack size ($\alpha$) and fracture toughness ($K_c$) as illustrated in the fracture mechanics triangle of FIG. 6.

Fracture toughness determination requires the testing of pre-cracked wire, for example, by notching the wire with a 1 mm notch. The notched wire specimen is then subjected to fatigue loading to induce a sharp crack at the root of the notch at a pre-set temperature. The wire specimen is then subject to axial tension until fracture. The crack size and applied stress at fracture are then used to evaluate fracture toughness.

After the fracture toughness ($K_c$) is evaluated, the ultimate capacity or strength of the cracked wire can be determined based on known relationships. This step is denoted at 30 in FIG. 1.

Figure 7:
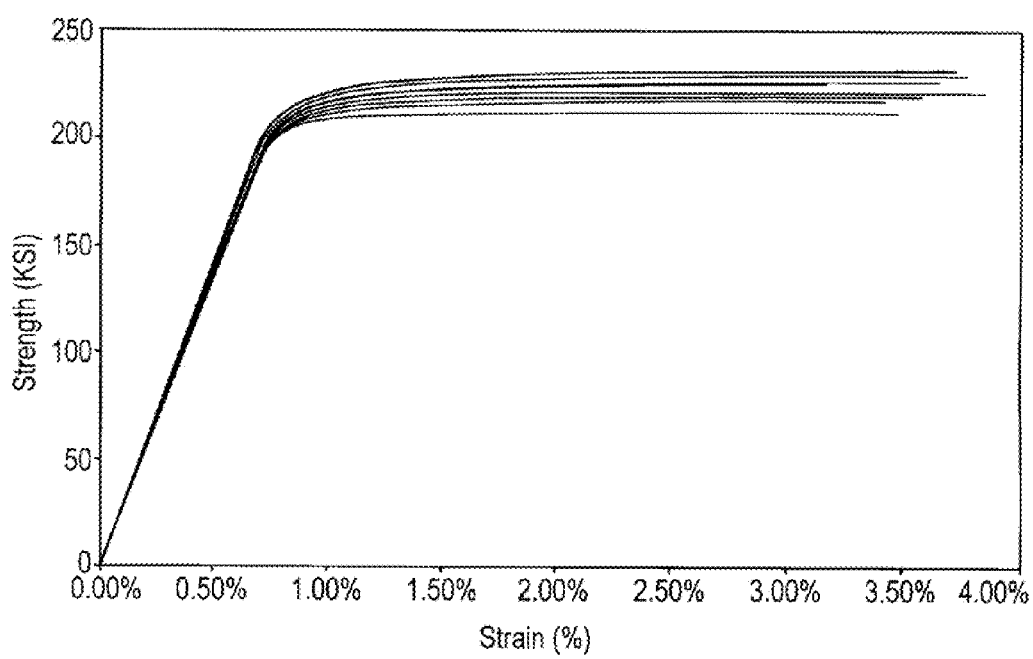
FIG. 7 is a typical stress strain curve showing for a group of wires produced by simulation.

From the above description it will be apparent that the input data for determination of the cable strength at any panel consists of the following:
 Test data for intact wires, $[\epsilon_e, E, \epsilon_u \sigma_u]_{Intact}$
 Test data for intact wires, $[\epsilon_e, E, \epsilon_u, \sigma_u]_{Cracked}$
 Probability of broken wires, $p_0$
 Probability of cracked wires, $p_1$
 Percentage of worst-wire population, $P_{worst}$
 Ultimate strength of cracked wires, $\sigma_{cracked}$ Based on test results for intact and cracked wires, incremental stress strain curves for each wire are simulated as typically illustrated in FIG. 7; this step is shown at 32 in FIG. 1.

All the wires in the cable cross-section are subjected to the same strain. The strain is applied incrementally up to the ultimate elongation of each individual wire, $\epsilon_u$, as determined from the respective wire stress strain curve. At each strain increment, the corresponding stress is determined from the stress strain curve for the wire. This process is repeated for each of the wires in the cable at each strain increment until all the wires reach their ultimate elongation. This step is denoted at 34 in FIG. 1. The load carrying capacity at each strain increment is summed up for all the wires. This sum represents the load carrying capacity for the cable at the given strain level. The process is repeated until the load carrying capacity for the cable reaches zero at maximum elongation as is noted at 36 in FIG. 1.

Figure 8:
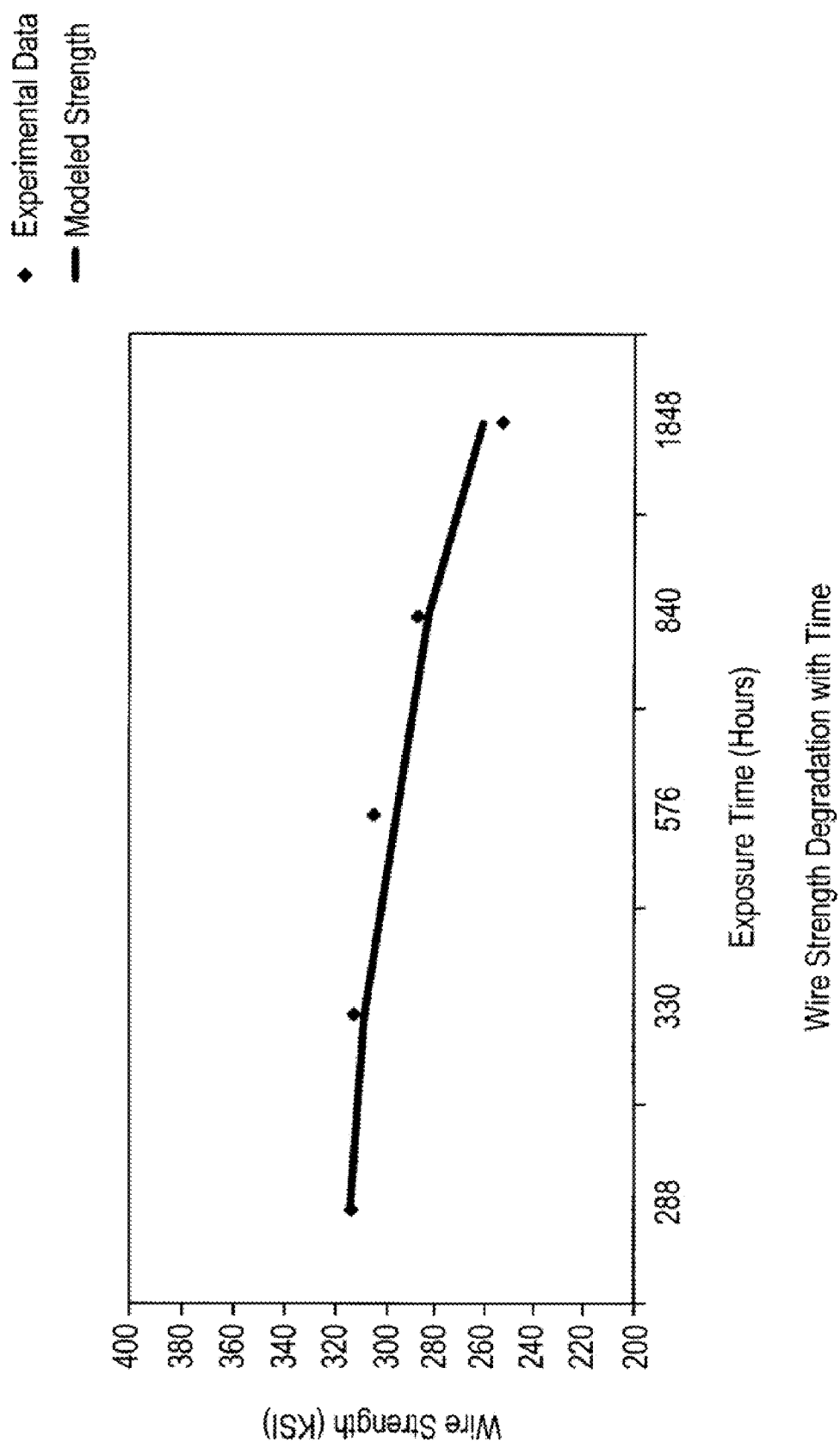
FIG. 8 is a graphical illustration showing a time-dependent degradation model.

The method of this invention also provides for an assessment of the remaining service life of the cable by determining the rate of change of broken wires detected by inspection over time and by measuring the rate of change of fracture toughness over said time frame and then applying a time-dependent degradation prediction model as shown in FIG. 8.

The fracture toughness is a critical component for determining the ultimate capacity of a cracked wire and is the parameter that characterizes the resistance of the material to brittle fracture. In the assessment evaluation of cable wires against fracture, the applied stress, crack size and fracture toughness, constitute the fracture mechanics triangle (shown in FIG. 6) and provide a mathematical relationship between the three variables. The wire material will sustain a crack without brittle fracture as long as the applied stress intensity factor is below the critical value of fracture toughness. However, environmental degradation will cause a reduction in the effective fracture toughness of the wire leading to brittle fracture at short crack depths. The effective fracture toughness, at short crack depth locations is significantly reduced due to environmental degradation. The effective fracture toughness is therefore utilized to predict the strength of degraded cracked wire.

It should thus be seen that there is provided an improved method for assessment of cable strength and residual life which achieves the various preferred objects of this invention and which is well adapted to meet conditions of practical use. Since many variations might be made of the present invention or modifications might be made to the exemplary method set forth above, it is to be understood that all materials shown and described with reference to the accompanying drawings are to be interpreted as illustrative and not in a limiting sense.

Having thus described the invention, there is claimed as new and desired to be secured by Letters Patent:

1. A simulation method for strength assessment of a cable having a plurality of wires comprising the steps of:
   a) inspecting the cable and obtaining a random sample of said wires in a panel of the cable including broken, cracked and intact wires;
   b) testing the wire samples in a laboratory under tension loading for determining mechanical properties including ultimate elongation and obtaining test results;
   c) determining a maximum elongation threshold based on the ultimate elongation of cracked wires within said sample;
   d) segregating the wires based upon the maximum elongation threshold into worst-wire and better-wire proportions;
   e) determining the probability of broken wires in the cable based upon the number of observed broken wires within the panel during inspection;
   f) determining the probability of cracked wires in the panel of the cable based upon the number of cracked wires in the said sample, as found from the laboratory test results;
   g) applying computational algorithms on the worst-wire proportion for establishing a distribution pattern of broken wires and cracked wires in the cable panel and for indirectly obtaining a distribution pattern of intact wires;
   h) developing a correlation matrix using the mechanical property variables for the intact and cracked wires in the said sample;
   i) simulating the mechanical variables to produce a model of the stress-strain relationship for the intact and cracked wires based on the properties in the said sample;
   j) applying fracture toughness criteria to the cracked wires for assessing ultimate strength of the cracked wires;
   k) applying incremental strain upon in the simulation model up to ultimate elongation of each wire and determining corresponding strength of each wire;
   l) summing up the load carrying capacity of the cracked and intact wires at each strain increment until load carrying capacity reaches zero at ultimate elongation of the entire cable.

2. A simulation method for strength assessment as claimed in claim 1 wherein the fracture toughness is determined by:
   i) notching a plurality of wire specimens;
   ii) applying fatigue loading to induce a sharp crack at the root of the notch for each wire specimen;
   iii) applying axial stress loading to fracture each wire specimen;
   iv) measuring the final crack size at ultimate strength; and
   v) determining the fracture toughness based on the relationship between the final crack size and the applied stress.

3. A simulation method for strength assessment of a cable as claimed in claim 2 wherein the fracture toughness is used to determine the current and time-dependent ultimate load capacity of a cracked wire.

4. A simulation method for strength assessment as claimed in claim 1 further including the step of:
   m) assessing remaining service life of the cable by:
      i) determining the rate of change of broken wires detected by inspection over a time frame;
      ii) measuring the rate of change of fracture toughness over said time frame to determine the strength of the cracked wires; and
      iii) applying degradation kinetics to assess the strength of the intact wires within a time-dependent degradation prediction model.

5. A simulation method for strength assessment as claimed in claim 1 including the step of utilizing fracture toughness for determining the extent of environmental degradation and the reduction in the strength of cracked wires.

6. A simulation method for strength assessment as claimed in claim 1 for determining wire strength reduction as a factor of environmentally assisted cracking, including the steps of:
   i) applying tensile loading to the specimen wire;
   ii) detecting wire ultimate elongation;
   iii) determining effective fracture toughness; and
   iv) utilizing effective fracture toughness to assess strength of degraded cracked wire.

7. A simulation method for strength assessment of a cable as claimed in claim 1 wherein the random sampling includes the steps of:
   i) removing the wrapping wires to expose the individual cable wires;
   ii) driving wedges into the exposed wires to define peripheral wedge openings in the cable;
   iii) determining the number of wires to be sampled at each wedge opening based upon a target for an acceptable level of error in estimated cable strength.

8. A simulation method for strength assessment of a cable as claimed in claim 7 wherein the wedges are driven into the cable to define a sampling frame having a depth of approximately 2-3 inches.

9. A simulation method for strength assessment of a cable as claimed in claim 7 wherein the peripheral wedge openings define a uniformly spaced eight wedge pattern.

10. A simulation method for strength assessment of a cable as claimed in claim 7 wherein the number of wires to be sampled is calculated to limit the acceptable level of error in the estimated cable strength.

11. A simulation method for strength assessment of a cable as claimed in claim 7 wherein the cable wires to be sampled are identified for removal based upon a computerized random number generator.

12. A simulation method for strength assessment of a cable as claimed in claim 1 wherein the distribution pattern of broken wires and cracked wires is established using a Monte Carlo simulation with the input variables being the probability of broken wires, the probability of cracked wires, and the percentage of worst-wire proportion to the total number of wires in the sample.

13. A simulation method for strength assessment of a cable as claimed in claim 1 wherein the wire samples are tested for the following mechanical properties; Young's Modulus (E); yield strength ($\sigma_e$); ultimate strength ($\sigma_u$), and ultimate elongation $\epsilon_u$.

14. A simulation method for strength assessment of a cable as claimed in claim 1 wherein the threshold elongation is determined in accordance with the following formula:

$$M_{threshold} = \mu + 2.58\sigma$$

wherein $\mu$ is the mean deviation and $\sigma$ is the standard deviation of the ultimate elongation of cracked wire samples.

15. A simulation method for strength assessment of a cable as claimed in claim 1 wherein the threshold elongation is assumed to divide the entire wire population into a worst-wire proportion having wires with an ultimate elongation below the threshold elongation and a better-wire proportion having wires with an ultimate elongation higher than the threshold elongation.

* * * * *